(12) United States Patent
Rathjen (10) Patent No.: US 8,858,539 B2
(45) Date of Patent: *Oct. 14, 2014

(54) OPHTHALMOLOGICAL APPARATUS FOR BREAKDOWN OF EYE TISSUE

(75) Inventor: Christian Rathjen, Bremen (DE)

(73) Assignee: Ziemer Holdings AG (CH)

( * ) Notice: Subject to any disclaimer, the term of this patent is extended or adjusted under 35 U.S.C. 154(b) by 899 days.

This patent is subject to a terminal disclaimer.

(21) Appl. No.: 12/526,715

(22) PCT Filed: Feb. 7, 2008

(86) PCT No.: PCT/CH2008/000045
§ 371 (c)(1),
(2), (4) Date: Aug. 11, 2009

(87) PCT Pub. No.: WO2008/098388
PCT Pub. Date: Aug. 21, 2008

(65) Prior Publication Data
US 2010/0094264 A1      Apr. 15, 2010

Related U.S. Application Data

(60) Provisional application No. 60/901,083, filed on Feb. 14, 2007.

(30) Foreign Application Priority Data

Feb. 14, 2007   (WO) ................ PCT/CH2007/000078

(51) Int. Cl.
*A61B 18/18*        (2006.01)
*A61F 9/008*        (2006.01)
*A61F 9/009*        (2006.01)

(52) U.S. Cl.
CPC ............. *A61F 9/008* (2013.01); *A61F 9/00827* (2013.01); *A61F 9/00825* (2013.01); *A61F 9/009* (2013.01); *A61F 2009/00897* (2013.01); *A61F 9/00836* (2013.01); *A61F 2009/00872* (2013.01)
USPC ............................................. 606/4; 351/205

(58) Field of Classification Search
CPC ............ A61B 3/00; A61B 3/10; A61B 18/18; A61B 18/00; A61B 18/20; A61F 9/00
USPC ...................... 606/4, 5, 10; 351/200, 205, 246
See application file for complete search history.

(56) References Cited

U.S. PATENT DOCUMENTS

| 5,364,390 A | 11/1994 | Taboada et al. |
| 2003/0208189 A1 | 11/2003 | Payman |

(Continued)

FOREIGN PATENT DOCUMENTS

| CN | 1891184 | 1/2007 |
| DE | 10 2005 001 249 | 7/2006 |

(Continued)

OTHER PUBLICATIONS

International Search Report dated May 27, 2008, issued in corresponding international application No. PCT/CH2008/000045.

(Continued)

*Primary Examiner* — James Greece
(74) *Attorney, Agent, or Firm* — Ostrolenk Faber LLP (57) ABSTRACT

An opthalmological apparatus for breakdown of eye tissue includes a base station with a light source for generating light pulses, a support arm, with an application head that can be placed onto an eye, is mounted on the base station. The light pulses are transmitted from the base station to the application head through an optical transmission system. The application head has a light projector for focused projection of the light pulses for punctiform breakdown of eye tissue. The support arm is of rigid design with horizontal orientation and has a hinge with a horizontally oriented rotation axis, the hinge is mounted in such a way that the application head can be placed onto the eye with a rotation extending about the rotation axis. The hinge permits controlled manual docking of the application head and light projector onto the eye in a vertical direction, via a rotation movement that is easy to perform and has minimal mechanical friction.

20 Claims, 8 Drawing Sheets

(56) References Cited

U.S. PATENT DOCUMENTS

| | | | |
|---|---|---|---|
| 2004/0254568 A1* | 12/2004 | Rathjen | 606/4 |
| 2007/0010804 A1* | 1/2007 | Rathjen et al. | 606/5 |
| 2008/0243107 A1 | 10/2008 | Muhlhoff et al. | 606/4 |
| 2012/0239014 A1 | 9/2012 | Rathjen et al. | 606/4 |

FOREIGN PATENT DOCUMENTS

| | | |
|---|---|---|
| EP | 1 486 185 A | 12/2004 |
| EP | 1 731 120 A | 12/2006 |
| JP | 2005-152505 | 6/2005 |
| JP | 2006-181358 | 7/2006 |
| JP | 2006-341103 | 12/2006 |
| WO | WO 89/06519 | 7/1989 |
| WO | WO 2007/056486 | 5/2007 |

OTHER PUBLICATIONS

International Search Report dated May 27, 2009 issued in PCT/CH2007/000078.

\* cited by examiner

OPHTHALMOLOGICAL APPARATUS FOR BREAKDOWN OF EYE TISSUE

CROSS REFERENCE TO RELATED APPLICATIONS

The present application is a 35 U.S.C. §371 National Phase conversion of PCT/CH2008/000045, filed Feb. 7, 2008, which claims benefit of International Patent Application No. PCT/CH2007/000078, filed Feb. 14, 2007, and of U.S. Provisional Application No. 60/901,083, filed Feb. 14, 2007, the disclosures of which are incorporated herein by reference. The PCT International Application was published in the English language.

BACKGROUND

1. Technical Field

The present invention relates to an opthalmological apparatus for breakdown of eye tissue. The invention relates in particular to an opthalmological apparatus that comprises a base station with a light source for generating light pulses, an application head that can be mounted on the base station by means of a support arm and can be placed onto the eye, with a light projector for focused projection of the light pulses, and an optical transmission system for transmitting the light pulses from the base station through the support arm to the application head.

2. Related Art

Instances of ametropia such as myopia (short-sightedness), hyperopia (long-sightedness or far-sightedness) or astigmatism can nowadays be permanently corrected by refractive surgical treatment. Refractive surgical treatments are surgical operations on the eye which change the optical refractive power of the eye with the aim of bringing it as close to a desired value as possible. One of the most important methods in refractive surgery is so-called laser-assisted in situ keratomileusis (LASIK) in which the interior of the cornea is removed with the aid of a computer-controlled excimer laser after a corneal flap has previously been partially severed and folded aside. To produce the corneal flap, use is made of mechanical microkeratomes in which a driven scalpel cuts the corneal flap. Recently, such corneal flaps have also been cut with the aid of strongly focused femtosecond laser pulses, which have pulse widths of typically 100 fs to 1000 fs (1 fs=$10^{-15}$ s). In addition to LASIK, there are further procedures for refractive correction that are performed on the cornea with the aid of femtosecond lasers. Such a system is marketed, for example, by IntraLase Corp, in Irvine, Calif., USA under the name of Pulsion FS Laser. In this system, a light source (femto laser) is located in a base station and is connected to an optical application head via an articulated mirror arm. In addition to the optical transmission system, a deflection system (scanner) and the light projector, the application head also comprises viewing means, such as camera or surgical microscope, and therefore has a considerable weight of several kilograms. For orienting and applying the light projector onto an eye of a patient, the entire application head is moved via linear translatory drives. The patient lies on a bed and does not move. For reasons of weight, the application cannot be done by hand, and motorized drives are necessary. To avoid applying excessive forces to the patient, the laser system comprises force-measuring systems in the vertical application direction.

Systems for cutting the corneal flap with focused femtosecond laser pulses are also marketed by Zeiss Meditec AG, with its Visumax, and by 20/10 Perfect Vision Optische Geräte GmbH, with its Femtec. In these systems, the light projector is connected fixedly to the base station. In these systems, the patient is oriented in the horizontal plane and also vertically with respect to the light projector with the aid of a patient bed. Therefore, these systems too cannot be applied manually onto the patient's eye. In addition, the special patient bed has to be integrated into the safety system of the laser system in order to avoid uncontrolled movements of the bed. The bed is thus part of the laser system and thus increases the system costs and the space required. A suitable choice of bed by the person using the system is not possible.

In the aforementioned systems, the docking of the light projector onto the patient's eye is first effected by orientation in the horizontal plane in the x-direction and y-direction (centring of the eye) and then by lowering or lifting the patient in the vertical z-direction.

EP 1731120 describes a system in which the application head is mounted flexibly on the base station via an articulated mirror arm composed of several arm elements and joints and permits manual application of the application head and light projector onto the eye of a patient. To permit the weight of the application head for manual application by means of the articulated mirror arm, the light projector has smaller lens systems compared to the previously known systems. In order to ensure that, despite the lens system of smaller dimensions, it is possible to work with focused laser pulses across an extensive work area on the eye, the application head additionally has movement drivers for moving the light projector in an advance direction and in a first scanning direction. An optical deflection to a vertical scanning direction is not possible, however. The limited work area permits only rapid positioning of the laser pulses within the work area. Limits are thus set on flexible positioning of the laser pulses across the entire eye.

SUMMARY

It is an object of the present invention to propose a novel opthalmological apparatus for breakdown of eye tissue, which apparatus avoids at least some disadvantages of the prior art. A particular object of the present invention is to make available an opthalmological apparatus for breakdown of eye tissue which enables manual application of the light projector onto an eye of a patient but permits a light projector with optics of high numerical aperture, which permits the focused projection of laser pulses in the whole viewable eye area both in the horizontal and also the vertical direction.

According to present invention, these objects are achieved in particular by the elements of the independent claims. Further advantageous embodiments are also set forth in the dependent claims and the description.

The opthalmological apparatus comprises a base station with a light source for generating light pulses, a support arm mounted on the base station, an application head that is mounted on the support arm and can be placed onto an eye and has a light projector for focused projection of the light pulses for punctiform breakdown of eye tissue, and an optical transmission system for transmitting the light pulses from the base station through the support arm to the application head.

The aforementioned objects are achieved in the present invention particularly by virtue of the fact that the support arm is of rigid design with a horizontal orientation and, at one end, has a hinge (in German "Drehgelenk") with an essentially horizontally oriented rotation axis, the hinge being mounted in such a way that the application head can be placed onto the eye with a rotation (rotation movement) extending about the rotation axis. The rigid support arm, i.e. designed in one piece and inherently immovable, permits a stable and simple connection of the application head to the base station. In particular, the rigid support arm and its constant, defined horizontal orientation make it possible to design the optical transmission system more simply than is the case, for example, with a multi-part articulated mirror arm. The hinge arranged horizontally on an end of the rigid support arm permits application of the application head or of the light projector onto the eye in the vertical direction via a preferably mechanically executed rotation movement, wherein the application head is guided on a kinematically generated arc, which permits a vertical movement component for placement onto the eye. The advantage of the rotation movement is its simple configuration and minimal mechanical friction. The support arm and the hinge thus permit controlled manual docking, i.e. application of the application head or light projector onto the eye, the user advantageously being able to employ his tactile senses in order to control the force or movement exerted via the tactile force and movement feedback. Because active systems for applying force and limiting force are unnecessary, increased safety is achieved only through the use of passive system elements. On account of the simply designed support arm and the actuators and sensors required only in small numbers, or not at all, a further simplified configuration and therefore lower costs are achieved. Moreover, the overall size of the components located directly over the patient can be reduced.

The hinge is preferably arranged on that end of the support arm directed away from where the support arm is mounted on the base station, and the application head is connected movably to the support arm via the hinge. By means of the movable arrangement of the application head on the rigid support arm via a hinge, the size and weight of the system part to be applied manually is reduced, which further facilitates the manual application and makes it controllable.

Preferably, the hinge is mounted in such a way that the application head can be rotated into a vertical position. Placing the application head in a vertical, upright position has the advantage that the light projector is easier accessible to an operator for maintenance or preparation, e.g. for cleaning, mounting alternative projection and/or contact elements, and/or attaching disposable protection covers.

In an embodiment, the apparatus comprises positioning means for rotary and/or translatory movement of the support arm parallel to a positioning plane for the positioning of the application head over the eye. The positioning means comprise, for example, guide rails and/or drive means for translatory movements in a horizontal positioning plane and/or hinges that permit a rotation (rotation movement) about a vertically extending rotation axis.

In an embodiment the horizontally oriented hinge is connected to the support arm via a further hinge. The further hinge has a vertically oriented rotation axis and enables a rotation of the application head about this vertical rotation axis. Using the vertically oriented hinge for connecting the horizontally oriented hinge to the support arm makes it possible to position and place the application head or the light projector, respectively, through simple and defined mechanical rotation movements about the vertical and horizontal axis. Furthermore, when placed in a vertical, upright position, the application head can additionally be rotated away from the patient towards the operator for easier maintenance and preparation operations.

In another embodiment, the support arm is connected movably to the base station via the horizontal oriented hinge, the hinge being implemented as a pivot hinge or a pivot joint, for example. The horizontally oriented rotation axis is aligned with the longitudinal axis of the support arm and enables a rotation of the support arm about its longitudinal axis. Thus, by rotating the support arm about its longitudinal axis, the application head or the light projector, respectively, can be placed onto the eye through a simple and defined mechanical rotation movement.

In an embodiment, the application head is connected to the support arm via a further hinge. The further hinge has a rotation axis oriented perpendicularly to the longitudinal axis of the support arm and enables a rotation of the application head about this vertical rotation axis. The hinge oriented perpendicularly to the support arm makes it possible to position the application head over the eye through rotary movement of the support arm.

In an embodiment the support arm is connected to the base station via a pivot joint having a vertically oriented rotation axis and enabling a rotation of the support arm about this vertical rotation axis. Connecting the support arm with the pivot joint to the base station provides a further degree of flexibility for positioning and placing the support arm and, thus, the application head and the light projector.

In an embodiment, the apparatus comprises beam-deflecting means arranged in the support arm and used for deflecting the light pulses in at least two scanning directions, and the light projector is dimensioned such that, without mechanical movement of the light projector, deflected light pulses can be projected in a focused manner across an entire working area of preferably 11 mm in diameter for breakdown of eye tissue.

In another embodiment, the application head has a viewing window permitting a top view of the eye in the projection direction of the light projector. The viewing window permits a top view of the eye by way of optical viewing or measuring modules, e.g. cameras, microscopes, measuring devices, which are connected movably to the base station or, alternatively, are independent from the base station. The optical viewing or measuring modules are oriented in the projection direction of the light projector and can be swivelled over the viewing window, or vice versa, while the application head is placed on or is being placed onto the eye. Moreover, the optical viewing or measuring modules can be swivelled away when not required. The possibility of optical viewing or measuring modules being able to be swivelled into and out of the line of sight above the eye means that the overall size and therefore the weight of the application head can be further reduced and its handling improved.

In an embodiment, weight compensation means are connected to the application head, in order to partially balance out the application head above the rotation axis in such a way that the application head can be placed onto the eye with an application force reduced by the inherent weight of the application head. By means of the only partially balanced out configuration of the masses involved in the rotation movement (application head and, depending on the design, the support arm), the application force on the eye can be generated by gravity. In an embodiment, the compensation means are adjustable by the operator, e.g. for full or exceeding compensation of the application head so that any force applied to the eye is provided manually by the operator.

In another embodiment, the light projector comprises a first lens system in a projection part of the application head oriented in the projection direction, and the light projector comprises a second lens system in a feed part of the application head angled away from the projection part and directed towards the support arm, said first and second lens systems being coupled via a deflecting mirror. The arrangement of the lens systems divided up into the projection part and feed part permits a reduction of the structural height of the light projector and thus of the application head. Moreover, external aids such as microscopes, cameras, visual aids onto which the patient can fixate his eyes and/or aiming aids, or measuring devices can be adapted more easily.

In an embodiment, the application head comprises a projection part oriented in the projection direction and a feed part angled away from the projection part and directed towards the support arm. The projection part is connected rotatably to the feed part, e.g. axially about a longitudinal axis extending through the feed part and/or about a transverse axis extending perpendicular to the longitudinal axis of the feed part. The rotatable connection of the projection part to the feed part allows light projector and securing means mounted thereon to be oriented precisely with the eye.

In another embodiment, the apparatus comprises a lock for fixing or releasing a rotation position of the application head about the rotation axis.

In one embodiment, the apparatus comprises height-defining means for determining a vertical position of the eye, and the base station comprises height-positioning means for setting a vertical basic position of the support arm. By setting a vertical basic position of the support arm, the rotation movement needed for vertical placement of the application head onto the eye can be reduced and thus be kept in an area closer to the vertical movement component, which on the one hand reduces the movement stroke necessary for the docking of the application head and on the other hand facilitates the horizontal orientation of application head and eye (centring).

In other embodiments, the application head has one or more grips and grip structures for manual handling, a contact body which can be placed onto the eye, is transparent at least in parts and is configured and arranged such that it sets a contacted area of the eye equidistant to a working surface, and securing means for fixing the application head on the eye by underpressure. The light source preferably comprises a femtosecond laser.

In a further embodiment, the apparatus comprises a column mounted on the base station. The support arm is mounted on the column, and the column is vertically movable for setting a vertical position of the support arm.

In an embodiment, the application head is formed as an elongated member. Integrated in the elongated member are counter-weights for balancing out at least partially the application head above the horizontally oriented rotation axis. For example, beam-deflecting means arranged in the elongated member can be used advantageously as counter-weights for balancing the application head. The elongated member is connected to the support arm via a hinge having a rotation axis oriented perpendicularly to the longitudinal axis of the support arm. The latter hinge enables lateral movement of the elongated member, and thus the application head, parallel to the longitudinal axis of the support arm.

BRIEF DESCRIPTION OF THE DRAWINGS

An embodiment of the present invention is described below by way of example. The illustrative embodiment is depicted in the attached figures, in which.

DETAILED DESCRIPTION OF THE EMBODIMENTS

Figure 1:
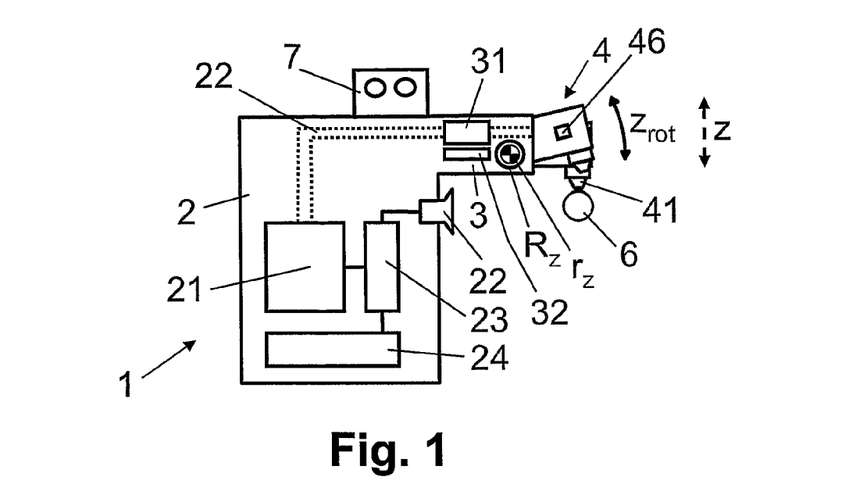
FIG. 1 shows a schematic side view of the opthalmological apparatus, comprising a one-piece design of a base station with a support arm on which an application head is mounted rotatably.

In FIGS. 1 to 6, as well as FIGS. 10 to 14, reference number 1 designates an opthalmological apparatus for breakdown of eye tissue. The opthalmological apparatus 1 comprises a base station 2 and an inherently rigid horizontal support arm 3 mounted thereon. For transporting the opthalmological apparatus 1, the base station 2 is provided with lockable rolls or wheels. An application head 4 is mounted on the support arm 3 fixedly or via a horizontally oriented hinge $R_z$. FIG. 1 also shows an optional optical viewing, imaging and/or measuring module 7 connected fixedly to the support arm 3, for example a monitor and/or a microscope for observing the application procedure (docking) and the treatment. In the embodiments according to FIGS. 1 to 6, 10, 13, and 14, the application head 4 is connected to the support arm 3 via the horizontally oriented hinge $R_z$ so as to rotate about the horizontal rotation axis $r_z$. The horizontally oriented hinge $R_z$ is in each case of these embodiments arranged at that end of the support arm 3 directed away from the connection of the support arm 3 to the base station 2. As is shown schematically in the side views in FIGS. 1 and 2, the hinge $R_z$ is arranged and configured such that, by the rotation $z_{rot}$ of the application head 4 about the rotation axis $r_z$, a vertical movement component can be executed in the z-direction for lowering and placing the application head 4 onto an eye 6. For manual handling, grips and/or grip structures 46 are mounted on the application head 4. In an embodiment, in order to keep the mass inertia low, and to reduce the number of the moved components, the rotation axis $r_z$ is arranged close to the patient. A person skilled in the art will understand that the rotation of the application head 4 about the rotation axis $r_z$ can also be effected by means of a parallelogram guide, for example, with further hinges $R_z$ being used for this purpose.

Although this is only shown schematically in FIG. 1, the opthalmological apparatus 1 in each case comprises a light source 21 (laser source) which is arranged in the base station 2 and generates light pulses, in particular a femtosecond laser for generating femtosecond laser pulses, and an optical transmission system 22 for transmitting the light pulses from the base station 2 through the support arm 3 to the application head 4. The opthalmological apparatus 1 preferably also comprises a lock 32 for fixing or releasing a position of rotation of the application head 4 about the rotation axis $r_z$, for example a friction coupling a catch or another engaging element that can be activated and released selectively.

Beam-deflecting means 31 are inserted into the optical transmission system 22 and are designed to deflect the light pulses in at least two scanning directions. A scanner suitable for the beam-deflecting means 31 is described in WO 2007/056486, for example. Galvanoscanners or acousto-optic modulators are also suitable. The beam-deflecting means 31 are preferably arranged in the support arm 3 and/or in the application head 4 in order to minimize the distance to the treatment area. For example, optical components for adjusting the (vertical) projection focus, e.g. a movable lens, are mounted in the support arm 3, while a galvanoscanner, for deflecting the laser beam in two (horizontal) scanning directions, is mounted in the application head 4. In an alternative example, the beam-deflecting means 31 include an additional high scanning device, mounted in the support arm 3, which allows for the superposition of a directionally adjustable microscan to the normal scan pattern, as described in EP 1 731 120, for example. The application head 4 comprises a light projector 41 with a lens system 42, 43 for focused projection of the light pulses into and/or onto the eye 6, in order to effect a punctiform breakdown of the eye tissue. The deflected light pulses are transmitted onwards by the optical transmission system 22 via the beam-deflecting means 31 to the light projector 41. The beam-deflecting means 31 and the light projector 41 are designed to scan a contiguous work area extending across the entire viewable region of the eye and to work with a focusing effect such that contiguous sections in the eye tissue, in particular in the cornea, can be cut. The beam-deflecting means 31 and the light projector 41 not only permit focused scanning of a plane work region, for example a horizontal work region, but, by targeted vertical positioning of the focus, also three-dimensionally defined work regions, for example vertical and curved sectional surfaces.

Although this is not shown in the figures, it should be noted that the application head 4 comprises a contact body which can be placed onto the eye 6, is transparent to light at least in parts and is configured and arranged such that it sets a contacted area of the eye 6 preferably equidistant to a work surface, and has securing means for fixing the application head 4 to the eye 6 by underpressure. Contact bodies can be plane or spherical, for example.

Figure 5:
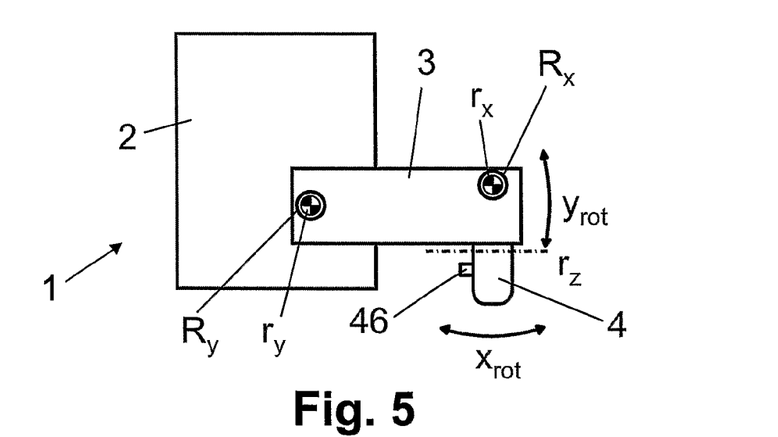
FIG. 5 shows a schematic top view of an opthalmological apparatus comprising a support arm which can be moved in rotation relative to the base station about a vertical axis of rotation in the positioning plane and on which the application head is mounted rotatably.
Figure 6:
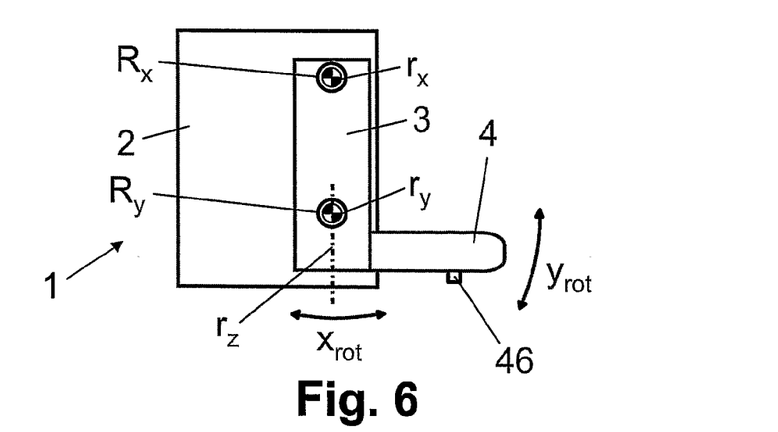
FIG. 6 shows a schematic top view of another opthalmological apparatus comprising a support arm which can be moved in rotation relative to the base station in the positioning plane about a vertical axis of rotation and on which the application head is mounted rotatably.
Figure 7:
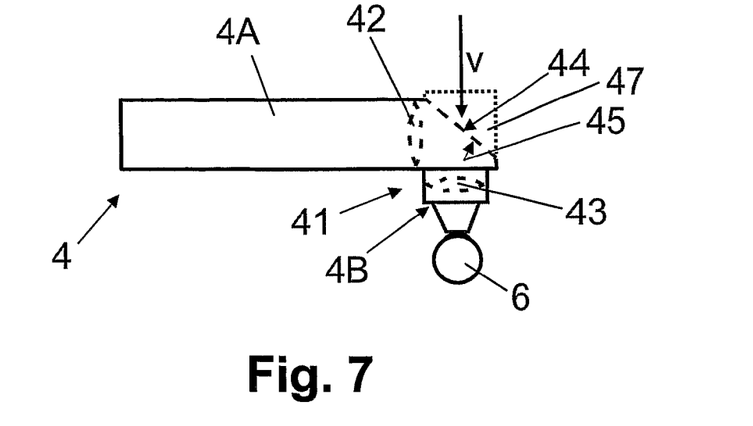
FIG. 7 shows a schematic side view of the application head, which comprises one lens system in a feed part to the support arm and another lens system in an angled projection part.

As is shown schematically in FIG. 7, the application head 4, in an embodiment that can be combined with FIGS. 1-6 and FIGS. 10-14, has a feed part 4A connected to the support arm 3, and a projection part 4B angled off from the feed part 4A. In this embodiment, the light projector 41 comprises a first lens system 43 in the projection part 4B and a second lens system 42 in the feed part 4A. The first lens system 43 and the second lens system 42 are coupled via the deflecting mirror 45. The application head 4 preferably also has a viewing window 44 permitting a top view of the eye 6 in the projection direction v. The viewing window 44 is designed, for example, such that the deflecting mirror 45 is transparent to light for the viewing wavelength. Reference number 47 designates coupling means, which are described in more detail below.

Figure 8:
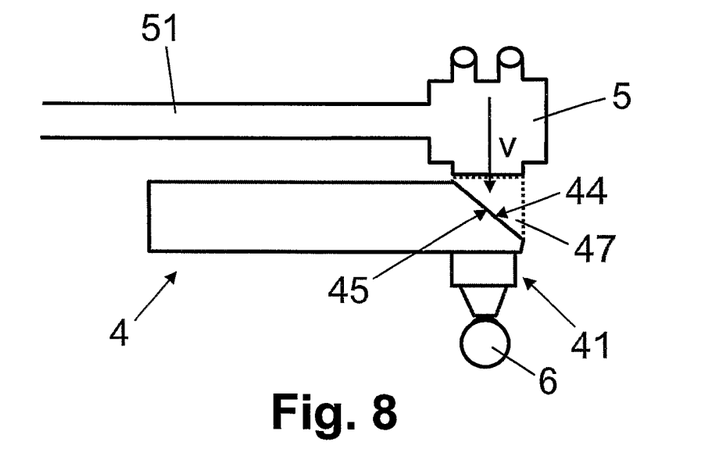
FIG. 8 shows a schematic side view of the application head, comprising a viewing window over the projection part, to which an optical viewing aid or measuring module is coupled in a releasable manner.

As is shown schematically in FIG. 8, the viewing window 44 permits optical coupling of optical viewing, imaging and measuring modules 5, e.g. a recording camera with optional pivotable monitor, which are mounted, for example by way of a module support 51, on the base station 2 so as to rotate about a vertically oriented rotation axis. These modules can thus be swivelled in and out over the application head 4, and their optical axes can be oriented with respect to the optical projection axis v of the light projector 41. The modules can additionally be mechanically connected to the application head 4 in a releasable manner via the coupling means 47, for example a detachable snap-fit catch or a bayonet catch. The coupling means 47 make it possible to connect mechanically and optically to the opthalmological apparatus 1 the optical viewing, imaging and measuring modules 5 placed over the viewing window 44. The additional weight of these add-on modules can be compensated by setting correspondingly the adjustable weight compensation means 33, e.g. the adjustable counter-weights 33'.

Figure 9:
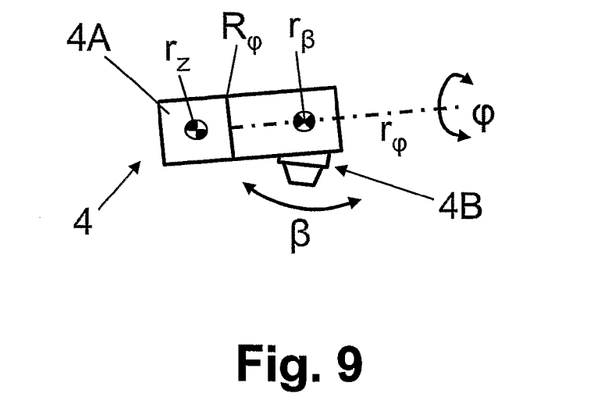
FIG. 9 shows a schematic side view of the application head, comprising a projection part connected rotatably to the feed part.
Figure 10:
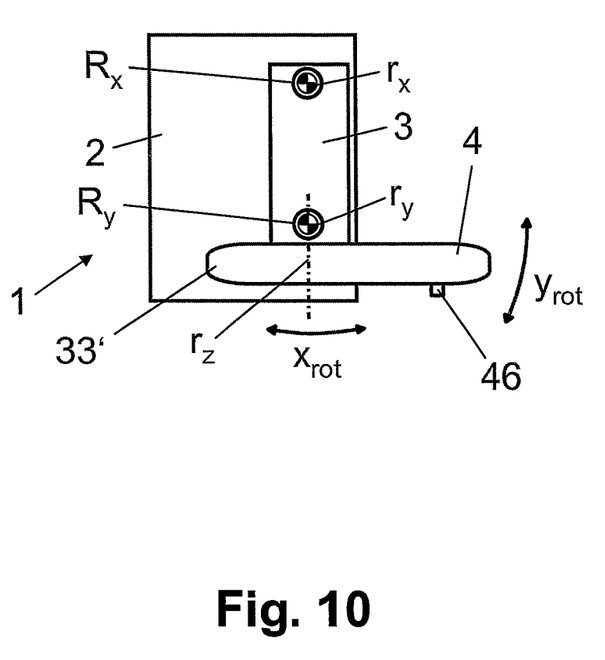
FIG. 10 shows a schematic top view of another opthalmological apparatus comprising a support arm which can be moved into a vertical, upright position through rotation.

In an optional embodiment that can be combined with FIGS. 1-8, and 10-14 and is shown schematically in FIG. 9, the projection part 4B is mounted pivotably on the feed part 4A. In the variant according to FIG. 9, the application head 4 has a hinge Rφ and the projection part 4B is rotatably connected with the angle φ about a longitudinal axis $r_p$ extending through the feed part 4A. The application head 4 additionally has a hinge $R_β$ and the projection part 4B is rotatably connected to the feed part 4A with the angle β about a transverse axis $r_β$ extending perpendicular to the longitudinal axis $r_φ$. Preferably, e.g. for mounting different projection objectives and/or contact and/or fastening elements, the opthalmological apparatus 1 comprises a lock for fixing or releasing the position of rotation of the projection part 4B about the rotation axis $r_φ$, for example a friction coupling, a catch or another engaging element that can be activated and released selectively.

In the embodiment according to FIG. 1, the support arm 3 is fixedly connected to the base station 2, for example the base station 2 and the support arm 3 are designed in one piece as an overall unit with a common housing. In this variant, the mutual orientation of eye and light projector 41, i.e. the centring of the light projector 41 to the eye 6, is effected by moving the patient's bed or the base station 2 in the x-direction and y-direction of a horizontal positioning plane (generally parallel to the ground surface on which the base station 2 is arranged).

Figure 2:
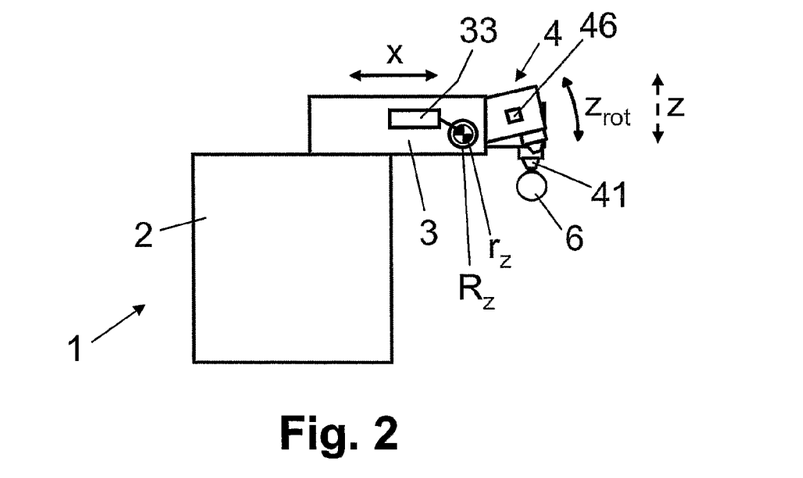
FIG. 2 shows a schematic side view of an opthalmological apparatus comprising a support arm which can be moved in translation relative to the base station in a horizontal positioning plane and on which the application head is mounted rotatably.
Figure 3:
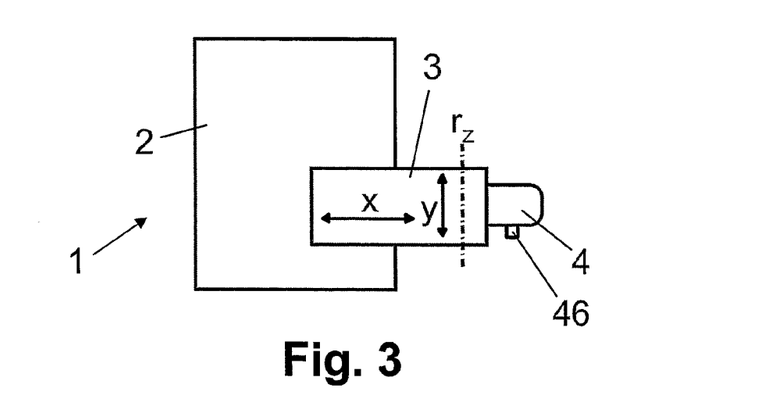
FIG. 3 shows a schematic top view of an opthalmological apparatus comprising a support arm which can be moved in translation relative to the base station in the positioning plane and on which the application head is mounted rotatably.

In the embodiment according to FIGS. 2 and 3, the support arm 3 is connected movably to the base station 2 such that the support arm 3, for orientation of the light projector 41 to the eye 6, can be moved in translation in the x-direction and y-direction of a horizontal positioning plane relative to the base station 2. The translatory movement is effected by means of translatory movement drivers or manually via corresponding guides.

Figure 4:
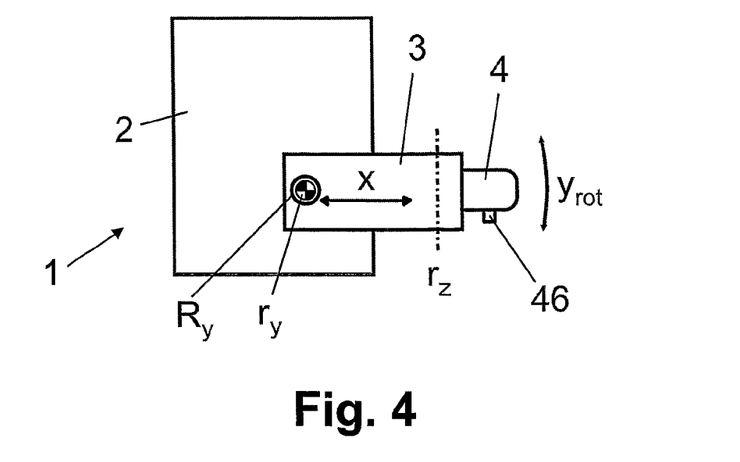
FIG. 4 shows a schematic top view of an opthalmological apparatus comprising a support arm which can be moved in translation and rotation relative to the base station in the positioning plane and on which the application head is mounted rotatably.

In the embodiment according to FIG. 4, the support arm 3 is connected to the base station 2 via the hinge Ry, e.g. a pivot hinge or pivot joint. The hinge Ry permits a rotation $y_{rot}$ of the support arm 3 about the vertical rotation axis $r_y$. As is shown schematically in FIG. 4, the hinge $R_y$ is arranged and configured such that, by the rotation $y_{rot}$ of the support arm 3 about the rotation axis $r_y$, a horizontal movement is permitted in the y-direction for orienting the light projector 41 to the eye 6. The orientation of the light projector 41 in the x-direction is effected by means of translatory movement, as in FIGS. 2 and 3.

In the embodiment according to FIG. 5, the orientation of the light projector 41 is effected by rotation both in the x-direction and also in the y-direction. In the embodiment according to FIG. 4, the application head 4 is connected to that end of the support arm 3 directed away from where the support arm is connected to the base station 2, in particular also via the hinge $R_x$. The hinge $R_x$ permits a rotation $x_{rot}$ of the application head 4 about the vertical axis $r_x$. As is shown schematically in FIG. 5, the hinge $R_x$ is arranged and configured such that, by the rotation $x_{rot}$ of the application head 4 about the rotation axis $r_x$, a horizontal movement in the x-direction is permitted for orienting the light projector 41 to the eye 6. The orientation of the light projector 41 in the y-direction is effected by means of a rotary movement, as in FIG. 4.

In the embodiment according to FIG. 6, the orientation of the light projector 41 is effected by rotation both in the x-direction and also in the y-direction, as in FIG. 5. In the embodiment according to FIG. 6, however, the hinge $R_z$ or rotation axis $r_z$ is turned through 90° in relation to the arrangement according to FIG. 5. The movement in the x-direction is effected by a rotation $x_{rot}$ of the support arm 3 about the vertical rotation axis $r_x$ of the hinge $R_x$, which connects the support arm 3 to the base station 2. The movement in the y-direction is effected by a rotation $y_{rot}$ of the application head 4 about the vertical axis $r_y$ of the hinge $R_y$ which connects the application head 4 to the support arm 3.

The positioning means for the rotatory and/or translatory movement of the support arm 3 for horizontal orientation of the application head 4 and of the light projector 41 with translatory movements in the x-direction and y-direction and/or with rotary movements $x_{rot}$ and $y_{rot}$ can be configured for manual movement and/or by means of movement drivers.

Although this is only shown schematically in FIG. 2, the opthalmological apparatus 1 comprises weight compensation means 33 which are connected to the application head 4, for example adjustable counter-weights 33', as illustrated in FIGS. 10 to 14, or springs. The weight compensation means 33 are preferably configured such that they only partially balance out the masses rotating about the rotation axis $r_z$, such that the application head 4 can be placed with a defined application force onto the eye 6.

Although this is only shown schematically in FIG. 1, the opthalmological apparatus 1 additionally comprises a control unit 23 arranged in the base station 2. The control unit 23 ensures that the beam-deflecting means 31 are not activated when the application head 4 is moved for placement onto the eye 6. The control unit 23 is also designed for controlling the beam deflection and for controlling and monitoring the movement drivers. The control unit 23 additionally comprises safety functions for monitoring of forces, movements and beam parameters.

In one embodiment, the opthalmological apparatus 1 moreover comprises height-defining means 22 for determining a vertical position of the eye 6, for example a camera or alignment laser beam(s) from a projector attached to the support arm 3, and the base station 2 comprises height-positioning means 24, e.g. translatory movement drivers, for setting a vertical basic position of the base station 2 and of the associated support arm 3. Thus, by setting the vertical position, the height-positioning means 24 make it possible to adjust the height of the horizontal positioning plane for the support arm 3. For a set vertical position, the support arm 3 is limited to defined horizontal movements through translation and/or rotation. The support arm 3 can be moved laterally at set heights but keeps an essentially horizontal orientation. The height-positioning means 24 are controlled, for example, by the control unit 23 on the basis of a vertical position of the eye 6 determined by the height-defining means 22. Manual setting of the basic position is also possible. By setting the basic position, the movement stroke required for the application head 4 can be reduced to 10-20 mm, for example. In the embodiments according to FIGS. 11 to 14, the support arm 3 is mounted on a column 8. The column 3 is vertically movable for setting the vertical position of the support arm 3. Preferably, at least in the embodiments of FIGS. 13 and 14, column 8 is connected to the base station 2 via a hinge $R_x$, particularly a pivot hinge or a pivot joint, and can be rotated about its vertical axis $r_x$.

In the embodiments according to FIGS. 10 to 14, attached to the application head 4 are counter-weights 33' for balancing the application head 4, as described above with reference to FIG. 2. Preferably, the application head 4 and the attached counter-weights 33' are formed as an elongated member 9.

The embodiments according to FIGS. 10-14 correspond essentially to the embodiment of FIG. 5 or 6. FIGS. 10-14 illustrate more clearly, however, that the elongated member 9 with the application head 4 and the attached counter-weights 33' can be rotated freely about the horizontal rotation axis $r_z$ without being blocked by either base station 2, support arm 3, or column 8. As illustrated in FIGS. 11 to 14, the base station 2 has a recess 25 for letting the elongated member 9 pass. At least, the elongated member 9 can be rotated into a vertical, upright position, whereby the counter-weights 33' are placed close to the base station 2 in the recess 25, and the application head 4 and the light projector 41 are on top, directed away from the base station 2. In the embodiments of FIGS. 10-14, the base station 2 can be positioned on the left or right hand side of the patient in that, through appropriate positioning of the elongated member 9, the application head 4 can be arranged over the patient's eye, either perpendicularly to or aligned with the patient's body. For example, in the embodiments of FIGS. 11 and 12, the application head 4 can be positioned on either side of the patient, either perpendicularly to or aligned with the patients body, by rotating the elongated member 9 about the vertically oriented rotation axis $r_y$. Alternatively, in the embodiments of FIGS. 10-14, through rotation of the elongated member 9 about the horizontal rotation axis $r_z$ in combination with a respective rotation of the projection part 4B about the longitudinal axis $r_\phi$, the application head 4 can be arranged over the patient's eye either perpendicularly to or aligned with the patient's body. Preferably, the opthalmological apparatus 1 comprises orientation detectors for determining individually or concurrently the orientation of support arm 3, elongated member 9, application head 4, and/or projection part 4B. The orientation detectors are connected to a processor which is configured to adjust and compensate settings of scanners, cameras and measurement modules based on the detected orientation.

In the embodiments of FIGS. 10-14 the elongated member 9 is connected to the support arm 3 via a hinge $R_y$ having a rotation axis $r_y$ oriented perpendicularly to the longitudinal axis of the support arm 3. The latter hinge $R_y$ enables lateral movement of the elongated member 9, and thus the application head 4, through rotation $y_{rot}$ about the rotation axis $r_y$. As is illustrated in FIGS. 11-14, the elongated member 9, including the application head 4 and the counter-weights 33', is arranged offset from the support arm 3 so that the elongated member 9 can be rotated freely about the rotation axis $r_y$ without being blocked by the support arm 3. To allow for free rotation of the elongated member 9 about the rotation axis $r_y$, while the elongated member 9 is in a vertical, upright position, the recess 25 is formed/bordered correspondingly with a rounded face 26.

Figure 11:
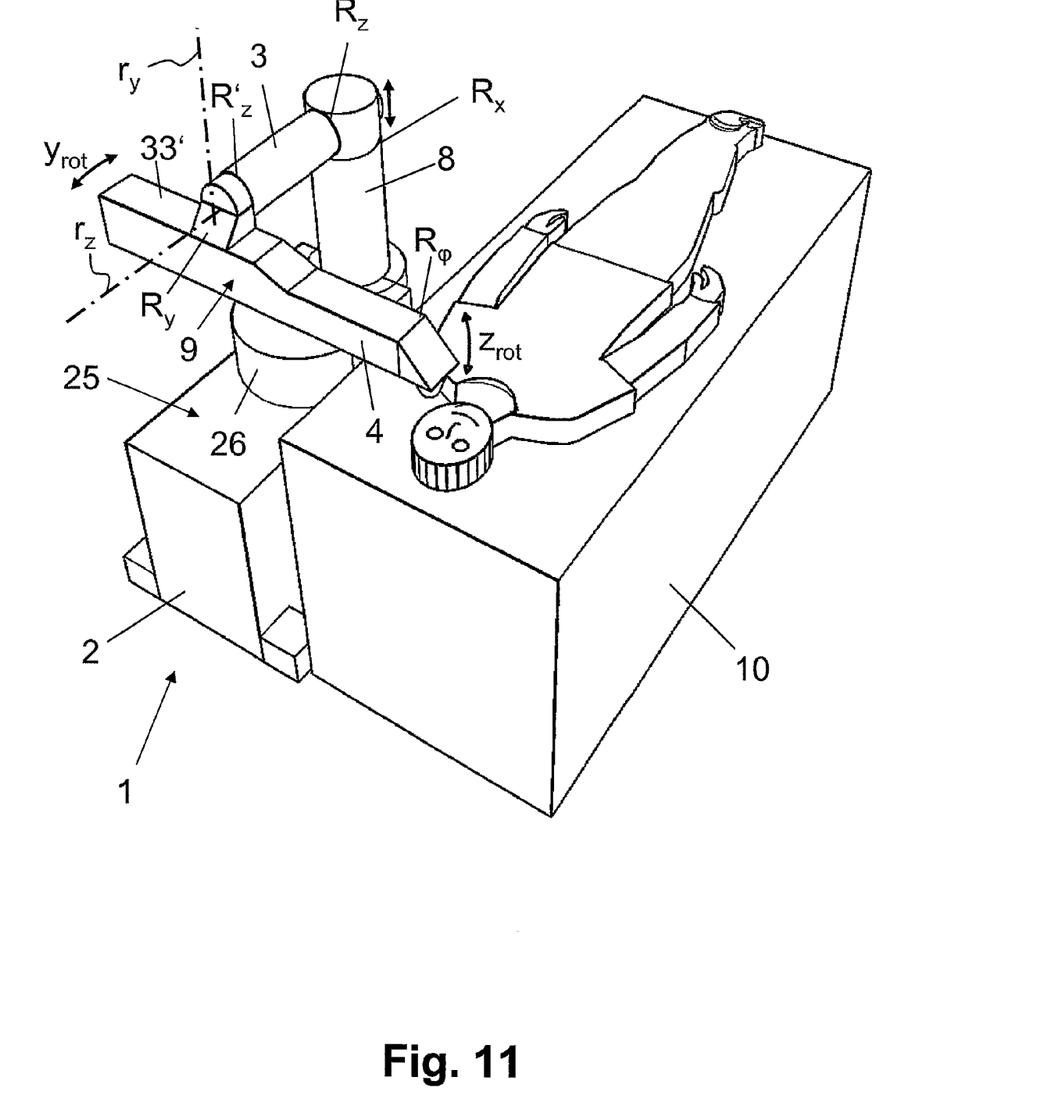
FIG. 11 shows a three-dimensional view of another opthalmological apparatus positioned next to a schematically illustrated bed with a patient.
Figure 12:
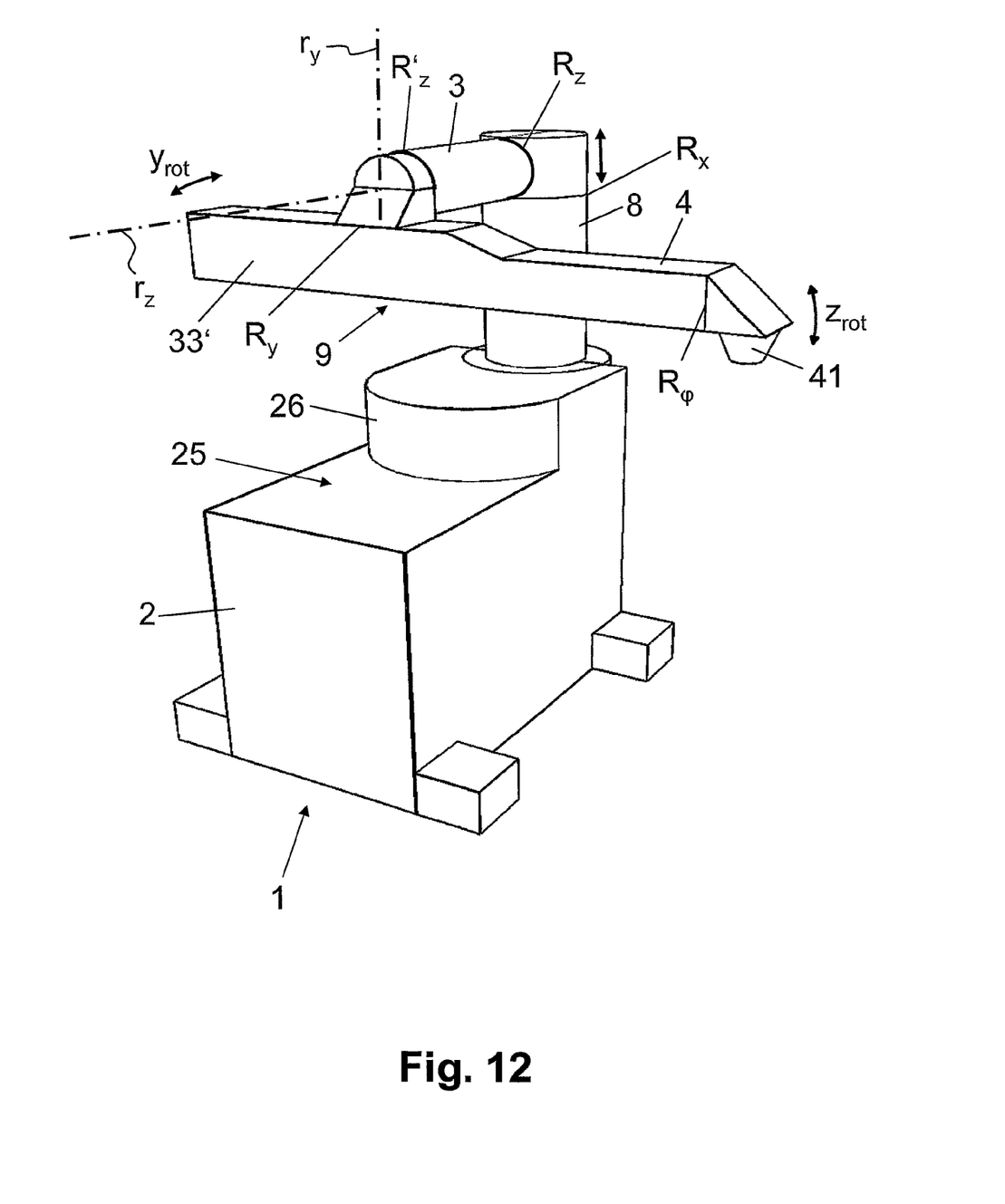
FIG. 12 shows a three-dimensional view of the opthalmological apparatus of FIG. 11, with a support arm that can be rotated about its longitudinal axis.

In the embodiment according to FIGS. 11 and 12, either the support arm 3 is connected movably to the base station 2, e.g. to column 8, via the horizontally oriented hinge $R_z$, e.g. a pivot hinge or a pivot joint, or, preferably, the elongated member 9 is connected to the support arm 3 via the horizontally oriented hinge $R_z'$ on the end of the support arm 3, directed away from where the support arm 3 is connected fixedly to the base station 2, e.g. to column 8. Essentially, the horizontally oriented rotation axis $r_z$ is aligned with the longitudinal axis of the support arm 3 and enables a rotation of the elongated member 9 about the longitudinal axis of the support arm 3. While the rotatable support arm 3 and/or a rotation of the elongated member 9 enable a rotation $z_{rot}$ of the application head 4 about the horizontal axis $r_z$, hinge $R_y$ enables lateral movement of the application head 4 parallel to the longitudinal axis of the support arm 3.

Figure 13:
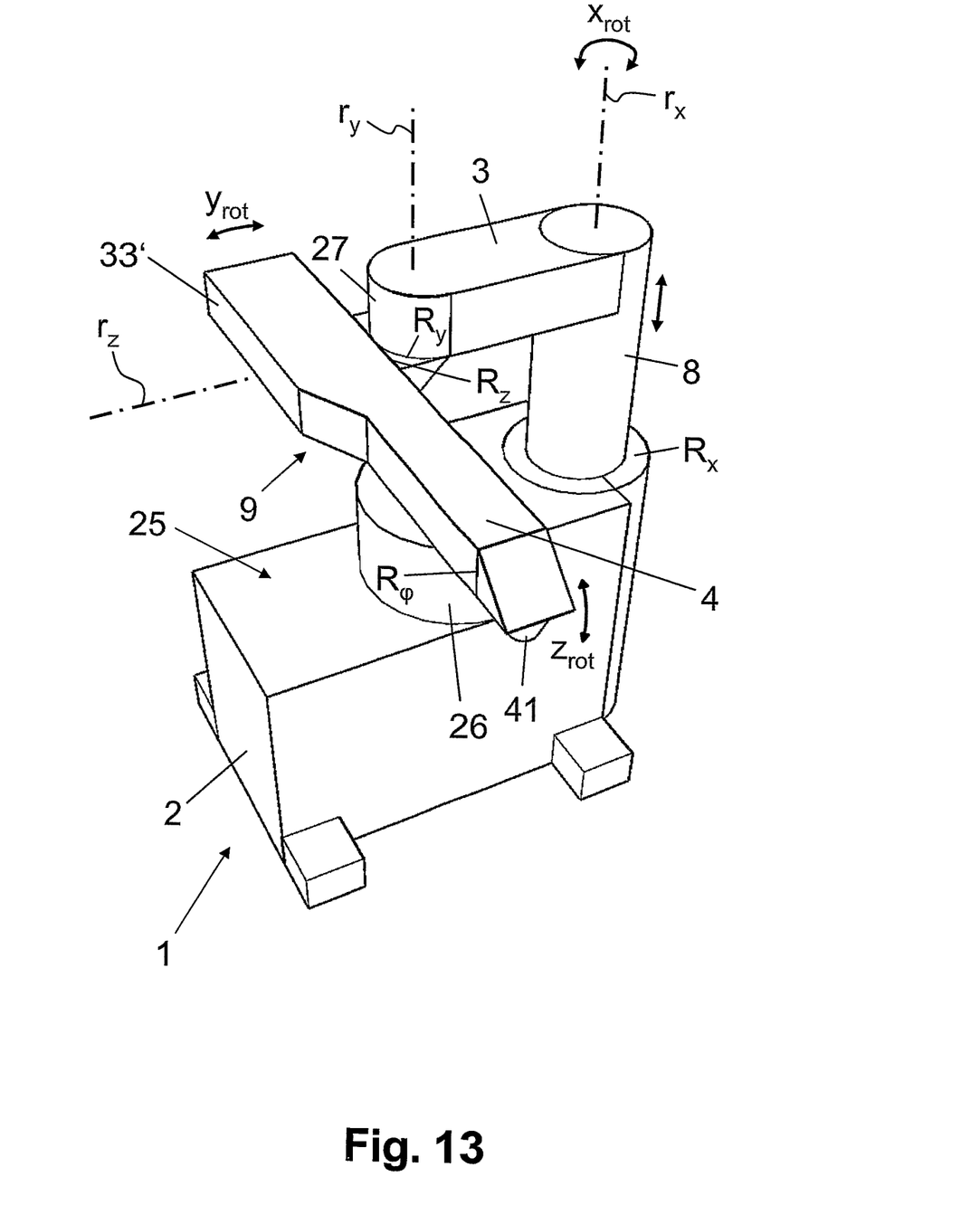
FIG. 13 shows a three-dimensional view of the opthalmological apparatus illustrated in FIG. 10.
Figure 14:
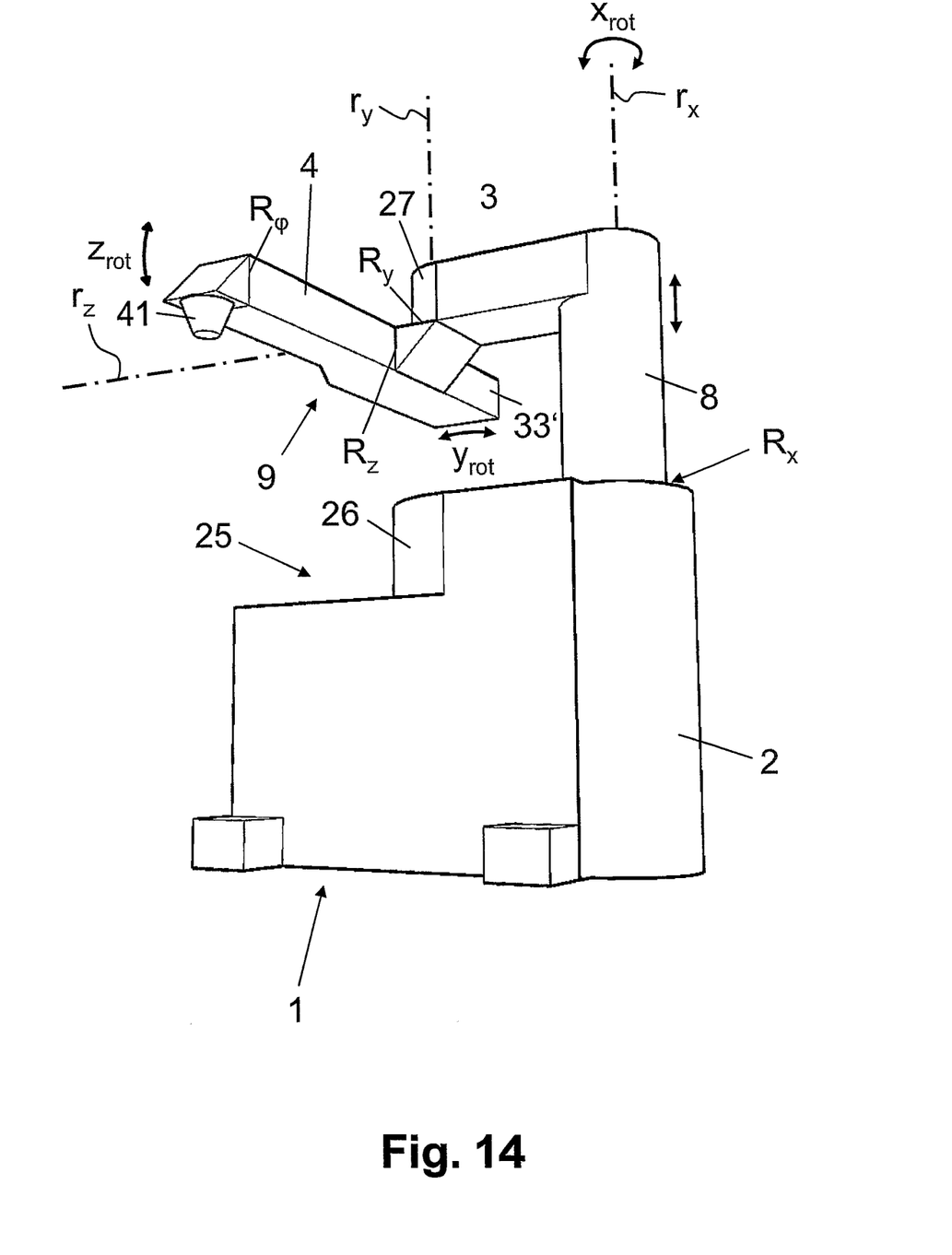
FIG. 14 shows a three-dimensional view of the opthalmological apparatus illustrated in FIG. 14 from a different viewing angle.

In the embodiment according to FIGS. 13 and 14, the support arm 3 is connected fixedly to the base station 2, e.g. to column 8. On the other end of the support arm 3, directed away from where the support arm 3 is connected to the base station 2, the elongated member 9 is connected to the support arm 3 via the horizontally oriented hinge $R_z$. The horizontally oriented hinge $R_z$ is connected to the support arm 3 via the vertically oriented hinge $R_y$ having a vertical rotation axis $r_y$ arranged perpendicularly to the longitudinal axis of the support arm 3. While the horizontally oriented hinge $R_z$ enables a rotation $z_{rot}$ of the application head 4 about the horizontal axis $r_z$, hinge $R_y$ enables lateral movement of the application head 4 parallel to the longitudinal axis of the support arm 3. To allow for free rotation of the elongated member 9 about the rotation axis $r_y$, while the elongated is in a non-horizontal position, the support arm 3 is provided with a rounded face 27.

Preferably, the opthalmological apparatus 1 comprises further locks for fixing or releasing a position of rotation of rotatable members about their respective rotation axis, specifically there are defined positions for transporting or parking the opthalmological apparatus 1 and for equipping the opthalmological apparatus 1 with different optical and/or mechanical components. Moreover, for manual handling and control, the opthalmological apparatus 1 comprises handles and/or gripping structures provided on the movable parts, particularly on the support arm 3, the elongated member 9, the application head 4, and/or the projection part 4B.

It shall be stated here that the term "hinge" is not intended to limit the scope of the invention, but to be as broad as the German term "Drehgelenk", i.e. a pivot joint connecting two mechanical bodies and enabling rotation of at least one of these bodies, relative to the other body, about a defined rotation axis.

What is claimed is:
1. Ophthalmological apparatus, comprising:
   a base station with a light source for generating light pulses,
   a support arm mounted on the base station,
   an application head that is mounted on the support arm and can be placed onto an eye and has a light projector for focused projection of the light pulses for punctiform breakdown of eye tissue, the light projector residing in an application head housing that is independent from the base station and the support arm,
   an optical transmission system for transmitting the light pulses from the base station through the support arm to the application head, wherein the support arm is of rigid design with a horizontal orientation and, at one end, has a hinge with an essentially horizontally oriented rotation axis, the hinge being mounted in such a way that the application head can be placed onto the eye with a rotation extending about the horizontal rotation axis; and
   a scanner arranged in the application head and configured to deflect the light pulse in at least two scanning directions, the scanner being configured to receive light from the light source and to transmit the received light to the projector.

2. Apparatus according to claim 1, wherein the hinge is arranged on that end of the support arm directed away from where the support arm is mounted on the base station, and in that the application head is connected movably to the support arm via the hinge.

3. Apparatus according to claim 1, wherein the apparatus comprises positioning means for rotary andor translatory movement of the support arm parallel to a positioning plane for the positioning of the application head over the eye.

4. Apparatus according to claim 1, wherein the hinge is connected to the support arm via a further hinge, the further hinge having a vertically oriented rotation axis and enabling a rotation of the application head about this vertical rotation axis.

5. Apparatus according to claim 1, wherein the support arm is connected movably to the base station via the hinge, and in that the horizontally oriented rotation axis is aligned with the longitudinal axis of the support arm and enables a rotation of the support arm about its longitudinal axis.

6. Apparatus according to claim 2, wherein the application head is connected to the support arm via a further hinge, the further hinge having a rotation axis oriented perpendicularly to the longitudinal axis of the support arm and enabling a rotation of the application head about this rotation axis.

7. Apparatus according to claim 1, wherein the support arm is connected to the base station via a pivot joint having a vertically oriented rotation axis and enabling a rotation of the support arm about this vertical rotation axis.

8. Apparatus according to claim 1, wherein the apparatus comprises beam-deflecting means arranged in the support arm and used for deflecting the light pulses in at least two scanning directions, and in that the light projector is dimensioned such that, without mechanical movement of the light projector, deflected light pulses can be projected in a focused manner across an entire work area for breakdown of eye tissue.

9. Apparatus according to claim 1, wherein the apparatus comprises beam-deflecting means arranged in the application head and used for deflecting the light pulses in the at least two scanning directions, and in that the light projector is dimensioned such that, without mechanical movement of the light projector, deflected light pulses can be projected in a focused manner across an entire work area for breakdown of eye tissue.

10. Apparatus according to claim 1, wherein the application head has a viewing window permitting a top view onto the eye in the projection direction of the light projector.

11. Apparatus according to claim 10, wherein the apparatus comprises one or more optical viewing or measuring modules which are connected movably to the base station and which, oriented in the projection direction of the light projector, can be swivelled over the viewing window.

12. Apparatus according to claim 1, wherein weight compensation means are connected to the application head, in order to partially balance out the application head above the horizontally oriented rotation axis in such a way that the application head can be placed onto the eye with an application force reduced by the inherent weight of the application head.

13. Apparatus according to claim 1, wherein the light projector comprises a first lens system in a projection part of the application head oriented in the projection direction, and in that the light projector comprises a second lens system in a feed part of the application head angled away from the projection part and directed towards the support arm, said first and second lens systems being coupled via a deflecting mirror.

14. Apparatus according to claim 1, wherein the application head comprises a projection part oriented in the projection direction, in that the application head comprises a feed part angled away from the projection part and directed towards the support arm, and in that the projection part is connected rotatably to the feed part.

15. Apparatus according to claim 1, wherein the apparatus comprises a lock for fixing or releasing a rotation position of the application head about the horizontally oriented rotation axis.

16. Apparatus according to claim 1, wherein the apparatus comprises height-defining means for determining a vertical position of the eye, and in that the base station comprises height-positioning means for setting a vertical basic position of the support arm.

17. Apparatus according to claim 1, wherein the application head has at least one of grips and grip structures, in that the application head comprises a contact body which can be placed onto the eye, is transparent to light at least in parts and is configured and arranged such that it sets a contacted area of the eye equidistant to a work surface, in that the application head has securing means for fixing the application head on the eye by underpressure, and in that the light source comprises a femtosecond laser.

18. Apparatus according to claim 1, wherein the apparatus comprises a column mounted on the base station, in that the support arm is mounted on the column, and in that the column is vertically movable for setting a vertical position of the support arm.

19. Apparatus according to claim 1, wherein the application head is formed as an elongated member, in that counterweights are integrated in the elongated member to at least partially balance out the application head above the horizontally oriented rotation axis, and in that the elongated member is connected to the support arm via a hinge having a rotation axis oriented perpendicularly to the longitudinal axis of the support arm.

20. Apparatus according to claim 1, wherein the hinge with the horizontally oriented rotation axis is mounted in such a way that the application head can be rotated into a vertical position.

* * * * *